United States Patent [19]

Thombre

[11] Patent Number: 5,431,921
[45] Date of Patent: Jul. 11, 1995

[54] DISPENSING DEVICE CONTAINING A HYDROPHOBIC MEDIUM

[75] Inventor: Avinash G. Thombre, Gales Ferry, Conn.

[73] Assignee: Pfizer Inc, New York, N.Y.

[21] Appl. No.: 987,282

[22] PCT Filed: Jul. 22, 1991

[86] PCT No.: PCT/US91/05018
§ 371 Date: Mar. 12, 1993
§ 102(e) Date: Mar. 12, 1993

[87] PCT Pub. No.: WO92/05775
PCT Pub. Date: Apr. 16, 1992

Related U.S. Application Data

[63] Continuation of Ser. No. 590,203, Sep. 28, 1990, abandoned.

[51] Int. Cl.⁶ ............................................. A61K 9/24
[52] U.S. Cl. ..................... 424/424; 424/425; 424/473; 424/426; 424/438; 424/494; 424/495; 424/497; 424/461; 424/462; 424/480; 424/482
[58] Field of Search ............ 424/486, 424, 425, 426, 424/494, 495, 497, 461, 462, 473, 480, 482, 438

[56] References Cited

U.S. PATENT DOCUMENTS

| | | | |
|---|---|---|---|
| 3,247,066 | 4/1966 | Milosovich, Jr. | 167/82 |
| 3,845,770 | 11/1974 | Theeuwes et al. | 128/260 |
| 3,995,631 | 12/1976 | Higuchi et al. | 128/260 |
| 4,111,202 | 9/1978 | Theeuwes | 128/260 |
| 4,160,020 | 7/1979 | Ayer et al. | 424/15 |
| 4,180,073 | 12/1979 | Michaels | 128/260 |
| 4,217,898 | 8/1980 | Theeuwes | 128/260 |
| 4,220,152 | 9/1980 | Dresback | 128/260 |
| 4,327,725 | 5/1982 | Cortese et al. | 128/260 |
| 4,350,271 | 9/1982 | Eckenhoff | 222/386.5 |
| 4,434,153 | 2/1984 | Urquhart et al. | 424/22 |
| 4,439,196 | 3/1984 | Higuchi | 604/890 |
| 4,553,973 | 11/1985 | Edgren | 604/892 |
| 4,612,008 | 9/1986 | Wong et al. | 604/892 |
| 4,642,233 | 2/1987 | Urquhart et al. | 424/19 |
| 4,747,847 | 5/1988 | Magruder et al. | 604/892.1 |
| 4,801,461 | 1/1989 | Hamel et al. | 424/467 |
| 4,927,633 | 5/1990 | Eckenhoff et al. | 424/438 |

FOREIGN PATENT DOCUMENTS

| | | |
|---|---|---|
| 0190969 | 1/1986 | European Pat. Off. |
| 0357369 | 8/1989 | European Pat. Off. |
| 2140687 | 12/1983 | United Kingdom |
| 2155787 | 12/1984 | United Kingdom |
| 9103235 | 8/1990 | WIPO |
| 9112795 | 9/1991 | WIPO |

*Primary Examiner*—Edward J. Webman
*Attorney, Agent, or Firm*—Peter C. Richardson; Gregg C. Benson; A. Dean Olson

[57] ABSTRACT

A device for the controlled delivery of an insoluble or partially aqueous insoluble beneficial agent to an aqueous containing environment. The device comprises a shaped wall that surrounds and defines an internal reservoir. The wall is formed at least in part of a sintered polymer microporous membrane permeable to a beneficial agent-containing hydrophobic medium when the wall is present in the aqueous containing environment. The reservoir contains a mixture of a hydrophilic swellable composition and a beneficial agent-containing hydrophobic medium.

9 Claims, 11 Drawing Sheets

DISPENSING DEVICE CONTAINING A HYDROPHOBIC MEDIUM

This was filed under 35 U.S.C. §371 based on PCT/US91/05018 filed on Jul. 22, 1991 which was a continuation of U.S. application Ser. No. 07/590,203, now abandoned, which was filed on Sep. 28, 1990.

This invention relates to devices particularly adapted for the delivery of a beneficial agent to an environment of use and methods for using the same.

BACKGROUND OF THE INVENTION

The desirability of controlled release of beneficial agents to an environment of use, such as the physiological fluid of animals (e.g. mammals) is known. Controlled delivery of beneficial agents such as drugs can, for example, result in a relatively constant concentration of such agents in the physiological fluids of an animal instead of the more dramatic rises and subsequent decreases in concentration of such agents usually associated with periodic dosing. Furthermore, controlled delivery of drugs can eliminate certain deleterious effects sometimes associated with a sudden, substantial rise in the concentration of certain drugs.

A variety of devices for the controlled delivery of beneficial agents have been described. Certain of those devises employ the physical phenomenon of diffusion for their operation. Examples of such diffusion driven devices are disclosed in U.S. Pat. No. 4,217,898. Other devices have been described which operate with the principle of colloidal osmotic pressure. Examples of such osmotically driven devices are disclosed in U.S. Pat. Nos. 3,845770; 3,995,631; 4,111,202; 4,160,020; 4,439,196 and 4,615,598. Devices which employ a swellable hydrophilic polymer which exerts pressure on a container forcing drug therefrom is disclosed in U.S. Pat. No. 4,180,073. U.S. Pat. No. 4,327,725 discloses a device which employs a layer of fluid swellable hydrogel to force beneficial agent out of the device through a specified and defined passageway. Other hydrogel powered devices containing such a passageway for delivery of beneficial agents are disclosed in GB 2,140,687A.

U.S. Pat. No. 4,350,271 teaches a fluid dispenser that operates by absorbing water. The dispenser includes a rigid water permeable housing, a water insoluble, water swellable composition that fills a segment of the space within the housing, a lipophilic fluid charge that fills the remainder of the space within the housing and that is immiscible in the water-swellable composition, and an outlet through the housing that communicates with the fluid charge. In operation the water swellable composition absorbs water, expands, and in piston-like fashion displaces the fluid charge from the dispenser via the outlet. Finally U.S. Pat. No. 4,434,153 discloses a delivery device comprising a hydrogel reservoir containing tiny pills which include a drug core surrounded by a wall.

Although the above inventions have advanced the art significantly there is a continuing search for other delivery devices particularly those which deliver water insoluble agents.

SUMMARY OF THE INVENTION

This invention is directed to a device for the controlled delivery of an insoluble or partially aqueous insoluble beneficial agent to an aqueous containing environment. The device comprises a shaped wall that surrounds and defines an internal reservoir. The wall is formed at least in part of a material, permeable to a beneficial-agent containing hydrophobic medium, when the wall is present in the aqueous containing environment. The reservoir contains a mixture of a hydrophilic swellable composition and a beneficial agent containing hydrophobic medium.

Other features and advantages will be apparent from the specification and claims and from the accompanying drawings which illustrate an embodiment of this invention.

DETAILED DESCRIPTION OF THE INVENTION

Figure 1:
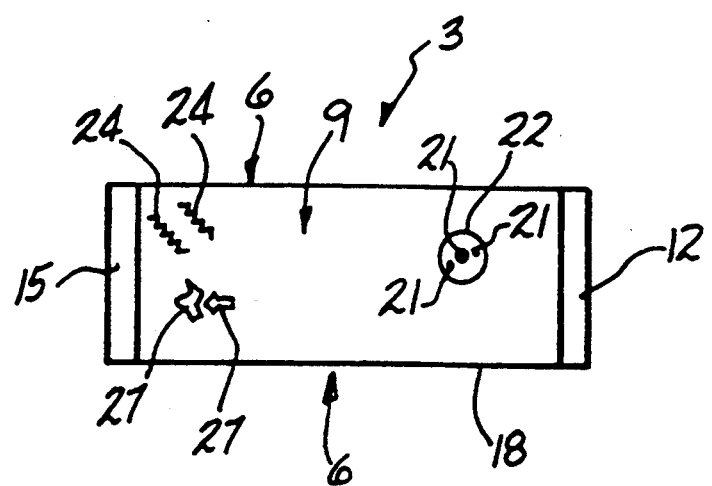
FIG. 1 illustrates a cross-section view of an exemplary dispensing device of this invention.

According to FIG. 1, dispensing device 3 comprises a Wall 6 that surrounds and defines an internal reservoir 9. At least some portion 12 of the wall 6 is permeable to the beneficial agent-containing hydrophobic medium (described below) and, if desired, to an aqueous medium. By permeable is meant that the beneficial agent either as a suspension or as a solution in the hydrophobic medium may pass through the wall 6. A variety of other wall portions (having different permeabilities to various components) may be combined with the beneficial agent permeable portion 12 as desired. For example part 15 of the wall 6 may be impermeable to the beneficial agent-containing hydropobic medium but is permeable to an aqueous medium. In addition, a portion 18 of wall 6 may be impermeable. Incorporation of these last two wall types are advantageous since if the whole wall is permeable to the beneficial agent then it typically must have other characteristics such as the appropriate water permeability and the appropriate mechanical strength. Incorporation of different wall portions facilitates achieving the different desired characteristics described above. For example the impermeable wall portion 18 can afford structural rigidity and robustness. In addition, for a device designed to be retained in the tureen of an animal, the impermeable wall portion 18 may provide the required density so that the device is not regurgitated. Also for example, for hydrophobic beneficial agents, it is easier to have a separate wall portion permeable to water than to have a single wall portion permeable to a hydrophobic medium and water.

The wall 6 thickness may be any dimension that provides the desired structural stability, effective resistance, and partitioning characteristics offered by the wall to transport of the desired species for the particular wall material chosen. For human health applications typical wall 6 thicknesses are from about 100 micrometers to about 2500 micrometers. Below about 100 micrometers a stagnant water film will control the transport properties instead of the membrane controlling them. Preferably the wall thickness is from about 100 micrometers to about 1000 micrometers because above about 1000 micrometers production may be more difficult. For wall portion 15 the flux of water through a water permeable wall is dependent on the gradient of chemical potential of water across the wall and on the resistance offered by the wall. The resistance offered by the wall, in turn, is a function of the effective mass transport coefficient, or, effective diffusivity of water through the wall, and its thickness and area.

The dispensing device 3 will vary based on the particular application (e.g. tablet). The shape may be modified (in conjunction with the desired wall portion characteristics) to change the diffusion rate of the device as different shapes are associated with different diffusion rates. Common exemplary shapes are cylindrical, tablet-shape, and capsular-shape. The dispensing device dimensions may vary with the desired application (e.g. cattle tablets, human tablets). The shape and size may also vary depending on the application so that for example the tablet is suitable for oral administration. The device dimensions vary depending on the quantity and rate of beneficial agent delivery which vary based on the application. However, typical dimensions range from about 0.4 inch to about 1 inch in length and about 0.1 inch to about 0.4 inch in diameter for human health appplications. For animal applications such as ruminal delivery to cattle typical dimensions range from about 3 inches to about 4 inches in length and about 0.8 inch to about 1.2 inches in diameter.

The wall 6 defines a reservoir 9 which contains a mixture of beneficial agent 21 in a hydrophobic medium 22, a swellable composition 24, and any other desired ingredients including for example, air 27. By mixture is meant two or more intermingled substances with each component essentially retaining its original properties. Thus, for example, the swellable composition retains its hydrophilic properties and the beneficial agent-containing hydrophobic medium (solution or suspension) remains hydrophobic.

The swellable composition 24 may be any composition that upon contact with an aqueous medium increases in size. By aqueous medium (i.e. aqueous containing environment) is meant a composition containing water as the principal liquid component (e.g. physiological fluids, solutions of organic or inorganic substances, particularly electrolytes, and mixtures of substances in water). Preferably hydrogels are used because of their desirable physical, chemical and mechanical properties. For example their solubility and extent of swelling (i.e. equilibrium water uptake), can be tailored by a variety of methods (e.g. (a) by modifying the chemical groups (alcoholic portion of pHEMA), (b) by copolymerization (HEMA and polystyrene or HEMA and poly (ethylene oxide), (c) by selecting the appropriate degree of crosslinking (the greater the degree of crosslinking the lower the solubility), and (d) by selecting the appropriate molecular weight and molecular weight distribution). However other swellable materials such as water-soluble polymers which hydrate, swell, and form gels before ultimately forming a solution may also be used (e.g. cellulose derivatives such as methycellulose, hydroxypropyl cellulose, hydroxypropylmethylcellulose, hydroxyethylcellulose, carboxymethycellulose and salts thereof; polyacrylic esters and polymethacrylic esters and copolymers; gelatin; copolymers of polyacrylic and polymethacrylic acid;polyethyleneoxide; and polyvinyl alcohol).

Hydrogels are known, for example, U.S. Pat. No. 4,327,725 the disclosure of which is hereby incorporated by reference, describes various hydrogels. The term hydrogel, as used herein, means at least one water swellable polymer that does not dissolve when exposed to water. Such hydrogels comprise polymeric materials which, when in contact with aqueous medium, absorb such water/medium and swell. Such absorption can be reversible or irreversible. Synthetic hydrogels are compatible with body fluids and have been investigated as biomaterials (e.g. contact lenses) and for controlled release applications.

The particular molecular weight of hydrogels employed in the devices of this invention are such that in conjunction with the amount of hydrogel the desired release rate through the coating is achieved. Preferably the polymers are noncrosslinked, although crosslinked polymers may be used, as this can obviate variation in the degree of crosslinking for different batches. In addition, as the crosslinking increases the swelling capacity reduces and the solubility reduces.

In addition it is preferred that the water swellable polymer is pelletized (in contrast to fine particles). By pelletized is meant increasing the size or granulating the swellable composition. This is because the gel, which results from the interaction between the pelletized polymer and water, inhibits transport to the portion of the device which is permeable to the beneficial agent formulation. If this transport occurs the permeability may be altered. For example, the gelled material can block the porous portion of the membrane and make it impermeable to the drug formulation (but permeable to water). However it is believed that the potential of altering the permeability of the membrane to the beneficial agent solution is critical only during the period immediately following the exposure of the device to an aqueous medium, (i.e. before the steady convective flow of the beneficial agent formulation through the appropriate portion of the device has been established). As the beneficial agent formulation is being delivered, the convective flow of the hydrophobic formulation may prevent transport of hydrophyllic materials into the beneficial agent permeable membrane. The gel may also inhibit transport of the swellable composition to the water permeable membrane wall portion and change its properties undesirably.

Thus, preferably the hydrogel phase (e.g. pellets) are of a size such that before or soon after gelling, they do not diffuse/migrate to the beneficial agent membrane. For animal health applications (e.g. ruminal delivery) pellets are typically from abut 0.125 inch to about 0.5 inch in diameter. For human health application pellets are typically from about 500 micrometers to about 2.5 millimeters or larger. Preferably for human health applications the pellets or granules are in the range from about 0.125 micrometers to about 1000 micrometers in diameter. The larger the size of the hydrogel phase, the lower will be its tendency to inhibit the movement of the beneficial agent formulation, and thus the phase is preferably larger than the pores available for beneficial agent permeability.

Exemplary hydrogels include gelled cellulose triacetate, polyvinyl alcohol, cellulose acetate, cellulose acetate butyrate, ethylcellulose, poly (hydroxyethyl methacrylate), poly (vinyl alcohol), poly (ethylene oxide), poly (N-vinyl-2-pyrrolidone), naturally occurring resins -such as polysaccharides (e.g. dextrans) and water-soluble gums, starches, chemically modified starches, and chemically modified cellulose. A preferred hydrogel is polyethylene oxide (PEO) because of its relatively large capacity to absorb water and swell, its availability in a variety of different molecular weights in commercial quantities, its biocompatibility, and its safety and favourable toxicity properties. PEO is commercially available and can be obtained having a variety of different molecular weights. For example, PEO can be obtained with nominal molecular weights of 8K, 14K, 100K, 400K, 600K, 1,000K, 1000K or 5,000K. A preferred molecular weight is about 400K to about 1,000K and an especially preferred molecular weight is about 500K to about 700K because of its advantages in providing a three to four week ruminal delivery device for cattle.

Another preferred hydrogel is polyvinyl alcohol (PVA) because of its relatively lower equilibrium swelling, and rate of swelling, which enables a long delivery duration of beneficial agent release. PVA is commercially available and can be obtained having a variety of different molecular weights and degrees of hydrolysis. For example, PVA can be obtained with molecular weights of 8K, 14K, 100K, 400K, 600K, 1,000K or 5,000K. A preferred molecular weight is about 100K to about 200K as this facilitates ruminal delivery for a duration of 100 to 150 days. In other applications where the delivery duration is shorter, other molecular weights will be preferred. A preferred degree of hydrolysis is about 75% to about 99.7% because of their ready availability.

The hydrogel employed can be a blend of, for example, two or more polymers. For example, different hydrogels comprising blends of PEO polymers of different molecular weights can be prepared and employed. Such blends can be adjusted to assist in achieving the desired delivery rates for the beneficial agents.

In addition to the hydrogel the delivery device contains a carrier for the beneficial agent (described below). The carrier is a hydrophobic medium. By hydrophobic is meant a substance which has a low affinity for water, (i.e. it is slightly soluble to insoluble in water, therefore it is not miscible in water or in an aqueous medium). The hydrophobic medium is critical to this invention as it is the carrier that allows delivery in contrast to an aqueous carrier). The hydrophobic medium viscosity is important since the average fluid velocity is inversely related to the fluid viscosity. Any hydrophobic medium viscosity may be used that in conjunction with the swellable composition, other components and membrane permeability pumps the beneficial agent at the desired rate. The viscosity may be varied as desired by the addition of additives (e.g. beeswax).

Hydrophobic mediums include all hydrophobic liquids and semisolids or solids. The active agent may be insoluble or soluble in the medium. It is preferred to use a hydrophobic medium that is a solvent for the desired beneficial agent in order to reduce settling of the suspended beneficial agent particles and thus causing variation in the drug concentration pumped out of the device. In contrast if beneficial agent solution stability is a problem, formulation of the beneficial agent as a suspension may be warranted. The consistency of the drug formulation can for example range from a low viscous liquid (e.g. up to 10 cp) to a "thick paste or semi-solid" at ambient temperature. Even a solid which becomes a flowable semi-solid or liquid at the temperature of the use environment may be used. Preferably the substance is a solid under ambient storage conditions and which becomes a flowable fluid at the temperature of the use environment as this facilitates formulation stability and desired shelf-life. Exemplary hydrophobic mediums include alcohols, soybean oils, isopropyl myristate, mineral oils, silicone oils, fatty alcohols, fatty acids, their esters, mono, di, and tri glycerides, and their mixtures, etc. Preferred hydrophobic mediums include silicone oils or polydimethylsiloxanes because they are physiologically inert, biocompatible, and available in a range of physical and chemical properties. Other preferred hydrophobic mediums include mineral oils (e.g. $C_{18}$ to $C_{24}$), refined or unrefined oils from plant or animal origin (e.g. soybean oil, coconut oil, olive oil), saturated or unsaturated fatty alcohols and their mixtures (e.g. octyl alcohol, lauryl alcohol, oleyl alcohol, and the like), esters of fatty acids (e.g. isopropyl myristate), fatty acids (e.g. oleic acid), esters of monohydric alcohols and fatty acids. In addition the hydrophobic medium may include other ingredients such as viscosity modifying agents (e.g. beeswax).

The above described carrier is used as a medium for the beneficial agents. The term beneficial agents includes for example any physiologically or pharmacologically active substance that produces a localized or systemic effect in animals. The term animals is meant to include mammals (e.g. human beings). The physiologically or pharmacologically active substances are sparingly soluble to insoluble in water. Indeed, an advantage of these devices is that such insoluble or partially insoluble substances can be delivered to the environment of use in a controlled fashion by the devices hereof. By insoluble is meant less than one part solute for 10,000 parts solvent. This invention is particularly adapted for delivering beneficial agents that are partially insoluble (i.e. a solubility less than one part solute to 30 parts solvent) and especially adapted for delivering beneficial agents that have a solubility range of about less than one part solute to 30 parts solvent and more than one part solute to 1000 parts solvent.

Examples of active substances include inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocold systems, alimentary and excretary systems, inhibitors of autocolds and histamine systems. The pharmaceutical agent that can be delivered for acting on these systems includes anti-depressants, hypnotics, sedatives, psychic energizers, tranquilizers, anticonvulsants, muscle relaxants, antisecretories, anti-parkinson agents, analgesics, anti-inflammatory agents, local anesthetics, muscle contractants, antibiotics, antimicrobials, anthelmintics, anti-malarials, hormonal agents, contraceptives, histamines, antihistamines, adrenergic agents, diuretics, antiscabietics, anti-pedicuIars, anti-parasitics, anti-neoplastic agents, hypoglycemics, electrolytes, vitamins, diagnostic agents and cardiovascular pharmaceuticals.

Also included in such active substances are prodrugs of the above-described drugs. Such drugs or prodrugs can be in a variety of forms such as the pharmaceutically acceptable salts thereof. However, a particular advantage of the devices of this invention is that such beneficial agents, such as the drugs and prodrugs described above may be delivered at the desired rate (e.g. controlled manner) in spite of poor solubility in water.

Devices of this invention are particularly advantageous for delivering two or more drugs simultaneously. The rate of drug release is controlled primarily by the rate of water influx into the device which is a function of the permeability of the device to water and the affinity of the composition within the device to water, and is relatively independent of the solubility of the incorporated drugs.

Thus two or more incorporated drugs can be released at absolute rates which depend upon their individual loadings in the device. For example, such devices can be used to co-deliver a sustained dose of an alphablocker, such as prazosin, and a diuretic, such as polythiazide, for the treatment of hypertension. For the treatment of cold symptoms, these devices can be used to deliver a combination of a decongestant, such as pseudephedrine hydrochloride, and an antihistamine, such as chlorpheniramine maleate or cetirizine hydrochloride. For treatment of cough/cold symptoms, three or more drugs can be released in a controlled fashion from such devices; for example a combination of an analgesic, a decongestant, and antihistamine, and an antitussive can be delivered. In addition the devices can provide controlled and sustained delivery of a wide variety of combination of drugs.

The term beneficial agent is also meant to include other substances for which it is desirable and/or advantageous to control delivery into an environment of use. Examples of such substances include, fertilizers, algicides, reaction catalysts and enzymes.

In addition other additives such as viscosity modifiers, antioxidants, stabilizers, pH controlling agents, flavoring agents, agents to improve the flow characteristics of the other components, suspending agents, lubricants, fillers, and the like may be added as desired to the mixture contained within the reservoir 9. Even gases (e.g. air) may be added to the reservoir for example to serve as a means of deliberately introducing a time-lag before beneficial agent delivery begins. When a device containing air is placed in the aqueous use environment, water influx into the device is initiated in response to the lower thermodymanic. activity of water within the device. Because of the swellable composition, there is an expansion in the volume of the device contents. However, beneficial agent delivery does not substantially begin until there is a compressible component present within the interior of the device. Hence the volumetric expansion is partly "used" by the device to compress/expel the air but not the beneficial agent formulation resulting in a time-lag. The amount of air present in the device can be controlled by selecting the appropriate level of nongaseous material in the interior of the device. The duration of the time-lag can be used in may beneficial ways. For example, it can be used to release the drug in the lower gastrointestinal tract similar to enteric dosage forms. It can also be used to deliver drugs in the jejunum, ileum, or even the colon, depending on the magnitude of the time-lag from the device, and the transit time of the device through the gastrointestinal tract.

Although any mixture of the above ingredients may be used that satisfactorily delivers (in conjunction with the device wall) the beneficial agent, typically the proportion of liquid to solid is determined from the equilibrium swelling properties of the swellable composition. Preferably the amount of swellable composition is such that $\geq 50\%$ of the internal space within the device is filled by the swelled composition so that at least about 50% of the beneficial agent formulation is released from the device by the pumping mechanism vs. other mechanisms (e.g. diffusion). The amount of beneficial agent is the amount that is sufficient to achieve the desired therapeutic effect. In addition the amount of air is such as to achieve the desired time lag. Thus, in human health applications an amount of air sufficient to achieve a 1–3 hour time lag for starting drug delivery in the jejenum and a 4–6 hour time lag for starting drug delivery in the colon is desired.

Any wall that is permeable to the beneficial agent containing hydrophobic medium and provides, or aids in providing, the desired beneficial agent release rate may be used. However it is preferred to use a wall that has a pore size of about 1 micron to about 100 microns because above about 1 micron the drug may be in solution or suspension and pass through the pores but below about 1 micron the drug must be in solution (because of particle size) to pass through the pores. Above about 100 microns there may be a large diffusive component, the mechanical strength of the membrane may be compromised, and, the internal pressure required for drug delivery may not be generated leading to uncontrolled release. The pores can be relatively nontortuous, uniform, and cylindrical; or, like a sponge or swiss-cheese, having an interconnected network of voids. This network can be complex with tortuous paths and with dead-end pores and occluded void spaces.

Suitable materials for this beneficial agent-containing hydrophobic medium permeable wall include microporous membranes such as sintered polymers, organic polymers, porous metals, and porous ceramics. Sintered polymers refers to thermally fused polymer particles. Typically sintered polymers have about 50% to about 99% porosity.

Exemplary sintered polymers include sintered polyethylene (PE), sintered polypropylene (PP), sintered polytetrafluoroethylene (PTFE), sintered polyvinylchloride (PVC) and sintered polystyrene (PS). Exemplary nonsintered film-forming polymers include cellulose acetate, ethylcellulose, silicone rubber, cellulose nitrate, polyvinyl alcohols, cellulose acetate butyrate, cellulose succinate, cellulose laurate, cellulose palmitate. Polymers which do not degrade significantly (i.e., break or burst) during the delivery period may also be used. Examples of such biodegradable polymers include polylactic acid, polyglycolic acid and poly (lactide-co-glycolide). Preferred beneficial agent permeable layers for animal health applications are sintered polymers such as PE, PP and PTFE used as a substrate (e.g. for impregnation as described below). For human health applications preferred beneficial agent permeable layers are nonsintered film forming cellulosic polymers.

In addition the beneficial agent-containing hydrophobic medium permeable wall portion may be impregnated with a variety of other additives as desired. For example the porous barrier may be impregnated with a low vapor pressure hydrophobic medium such as those described above. This aids in providing control of the rate of transport of species such as the beneficial agent-containing hydrophobic medium. All or part of the porous barrier may be treated.

Alternatively the pores may be impregnated with a hydrophilic hydrogel such as the hydrogels described above (e.g. gelled cellulose triacetate) which facilitates tailoring of the wall properties (e.g. diffusion rates), provides mechanical strength to prevent pore collapse, prevents leakage of beneficial agent formulation and the like. In order to facilitate diffusion of beneficial agent-containing hydrophobic medium the hydrogel may be wetted with a low vapor pressure hydrophobic medium such as those described above (e.g. lauryl alcohol). In addition instead of wetting the hydrogel with a hydrophobic medium it may be wetted with a hydrophilic medium (described hereafter) and at least one hole provided therethrough to allow beneficial agent-containing hydrophobic medium diffusion. This facilitates for example the further tailoring of the diffusion rate. Any hydrophilic medium that facilitates the diffusion of the beneficial agent may be used. Typically the hydrophilic medium is a low to moderate molecular weight, high viscosity, low vapor pressure liquid. Exemplary polymers are the polyethylene glycols, propylene glycols and glycerols.

The aqueous permeable membrane typically comprises the same structures as described above (for the beneficial agent-containing hydrophobic medium permeable wall (e.g. pore size, composition of sintered polymers, nonsintered polymers)). In contrast however the aqueous permeable membrane is impregnated with different materials to achieve the desired aqueous permeability. Thus, the aqueous permeable membrane may be filled with a hydrophilic medium such as those described above (e.g. Polyethylene glycol). Alternatively, the pores may be impregnated with a hydrogel such as those described above and wetted with a hydrophilic medium such as those described above to prevent drying out of the hydrogel in order to make the barrier permeable to water. The rate of transport of an aqueous medium through the membrane barrier depends on the difference in the thermodynamic activity of water on either side of the barrier, and the resistance offered by the barrier (i.e. the effective barrier thickness, the area available for transport, and the like). The gel in the pores is not released from the device because it is present in a swollen state. Alternately, it can be crosslinked, in order to prevent its release. The polymer can be incorporated as the polymer or as the monomer and then polymerized in situ. A wetting agent imparts stability to the incorporated hydrogel. Thus for example PEG-400 prevents the drying out of gelled cellulose triacetate and imparts stability and shelf-life. Generally the wetting agent should be of a viscosity and volatility that is not lost during the maximum shelf-life of the product.

The above permeable layers can also comprise one or more porosigens such that, when the devices are placed in an environment of use, the porosigens dissolve and effect the formation of a plurality of pores in and through the desired coating.

As stated above, the porosigens can be employed alone or in combination to effect formation of the pores in and through the coating. The ratio of porosigen to coating polymer can be varied as well as the choice of porosigens to be employed. Such variations are known and will be determined by such factors as the solubility of the beneficial agents, the particle size of the agents, the molecular weight of the hydrogel and the desired rate of release. Examples of porosigens which will function to form the pores in and through the coating include inorganic salts such as sodium chloride, potassium chloride, potassium phosphate. Other effective porosigens are particulate organic compounds and salts thereof such as glucose, sucrose, lactose, succinic acid, sodium succinate, sodium carbonate. Also effective porosigens are water-soluble polymers such as polyethyleneglycol (PEG), hydroxypropyl cellulose (HPC), and polyethylene oxide (PEO). Preferably such pore-forming polymers have the ability to form a phase-separated coating when mixed with the coating forming polymer of this invention. That is to say, preferably the porosigen polymer and the coating polymer are not totally miscible. Combinations of porosigens such as particulate organic compounds and salts thereof with inorganic salts and/or water-soluble polymers can also be employed. Similarly, inorganic salts with water-soluble polymers can be employed as porosigens. When the devices are to be used to deliver beneficial agents to an animal, the porosigen or porosigens employed must be pharmaceutically acceptable.

In addition to the formation of pores upon placement of the devices of this invention into an environment of use through dissolution of one or more porosigens, the pores can be preformed. Such preformed pores can be produced by known methods such as by gas generation in the coating during formation of the coating; etched nuclear tracking; laser, sonic or mechanical drilling; or electric discharge. It is preferred, however, that such pores result from dissolution of porosigen as described above.

The devices of this invention may also utilize an impermeable wall portion which is typically comprised of high strength, corrosion resistant metals such as stainless steel in order to impart the desired density for ruminal delivery applications.

In addition to the above-mentioned ingredients of the devices of this invention, other common pharmaceutical excipients may be present. Examples of such excipients include, binders such as microcrystalline cellulose, plasticizers such as polyethyleneglycol-600, and buffers such as sodium phosphate.

The devices of this invention can also be administered within a capsule comprising a water soluble wall. For example, the devices can be manufactured to be of suitable size for inclusion either singly or multiply within a gelatin capsule such that when the capsule dissolves the device(s) are released into the environment of use. While the devices to be included within a capsule can be of a variety of shapes, a preferred shape for such devices is spherical or substantially spherical. The exact number and size of such devices can and will be determined according to a variety of well known factors. For example, the environment of use, the beneficial agent or agents, the amount of beneficial agent and the rate of release are all factors to be considered in determining the size, shape, and number of devices to be included in such capsules as well as the composition of the capsule.

The devices of this invention having the above described desired characteristics may be made using the above described materials using conventional methods. For example, in general capsules may be produced by forming a cap and body of sintered polymers. Typically the desired polymers are molded into the desired shapes and sintered. Either the cap or the body is made permeable to water and the other is made permeable to the beneficial agent-containing hydrophobic medium. A solution of the desired impregnating material (e.g. cellulose triacetate) is imbibed into the porous sintered structure by differential pressure application. The impregnated sintered structure is wetted if appropriate by for example equilibriating in a bath of the wetting agent. If appropriate a hole is drilled through the wetted gelled impregnated structure by mechanical or laser drilling. The beneficial agent, swellable composition and other ingredients are placed into the structure as a mixture or in succession leaving room for the desired amount of air. Then the capsule is assembled and if desired joined by conventional methods used for gelatin capsules. Preferably water insoluble joining methods are used since if the capsule comes apart it may not function in the desired manner. For ruminal applications an impermeable wall portion may be joined between the cap and body portions.

Tablets may be made for example by compressing blends (using conventional tabletting methods) of the beneficial agent-containing hydrophobic medium, swellable composition and other additives to form a tablet core. This tablet core is coated with the desired porous polymeric barrier using conventional pan or fluidized-bed coating techniques. Alternatively by dipping a suitably shaped-tablet core partly in a hydrophobic polymer solution and partly in a hydrophilic polymer solution a tablet having a beneficial agent-containing hydrophobic medium permeable wall portion and an aqueous medium permeable wall portion may be made.

Granules may be made by forming the desired composition by extrusion-spheronization or fluid-bed granulation. The thus formed particles are coated with the desired porous polymeric barrier by conventional pan or fluidized-bed granulation.

Methods for using the devices of this invention include administration of the appropriate devices to animals via oral administration or by insertion of the appropriate devices into a body cavity of the animal. Devices of this invention can,also be used to deliver agents to such environments of use as fish tanks, soil and aqueous chemical and/or enzymatic reaction systems. In such cases, the devices are placed into the desired environment of use. The devices of this invention require that such environment of use be either aqueous or provide for contact of the device with water or other aqueous medium.

In spite of the many advancements made in the design and manufacture of drug delivery devices, the development of a device for ruminants such as cattle, and for humans, which is able to deliver a relatively poorly water-soluble (1 to 50 ug/mL) drug of moderate molecular weight (up to 500 daltons) remain a challenge to the delivery device designer. Utilizing the diffusion-dissolution of the drug through a polymeric membrane or matrix as a mechanism to control the drug release rate is limited by the relatively low flux of drug that can be achieved using commonly available and pharmaceutically acceptable polymers. This eliminates an important class of drug delivery devices. Devices based on the chemical or physical erosion of polymers are not suitable, particularly for drugs with a narrow therapeutic index, if the erosion cannot be restricted to the surface of the device. Thus, the choices of drug delivery technologies available for a large number of therapeutic agents which are poorly water soluble are limited. The device of this invention will be primarily useful for delivering drugs that fall into this category, and in particular, drugs which can be dissolved/dispersed in an oily vehicle, mixed with the second phase consisting of a water-swellable composition, and surrounded by a barrier with suitable permeability characteristics.

EXAMPLE 1

Construction of the Delivery Device and Characterization of the Drug Release Profile Prototype delivery devices were made from a stainless steel cylinder of nominal diameter 21.8 mm and nominal length 77 mm. Each device contained 6 grams poly (ethylene oxide) having an average molecular weight of 600,000 daltons (Polysciences) and about 28 ml of a 5% solution of the ionophore CP-53,607 in octyl alcohol. The total drug load in the device was 1380 mg. The poly (ethylene oxide) polymer was present in the device in the form of pellets made by compressing 60 mg of the polymer on a type "F" tabletting machine with 5/32" flat-face tooling. The device was capped at one end with sintered polyethylene disc impregnated with cellulose acetate and wetted with PEG-400. The other end of the device was capped with a porous (unimpregnated) sintered polyethylene disc. The release medium (dissolute medium) consisted of 300 ml of 0.1M phosphate buffer at pH 9.0 and 100ml of octyl alcohol in a 1000 ml flask. The organic phase (octyl alcohol) was present as a distinct layer above the aqueous phase (phosphate buffer). The device was lowered gently into the flask kept on a laboratory shaker at room temperature. The device was completely immersed in the aqueous layer throughout the release rate testing period. Every six to seven days, the media in the dissolution flask were replaced with fresh solutions. The drug released into the aqueous and organic layers was assayed by UV spectrophotometry.

Figure 2:
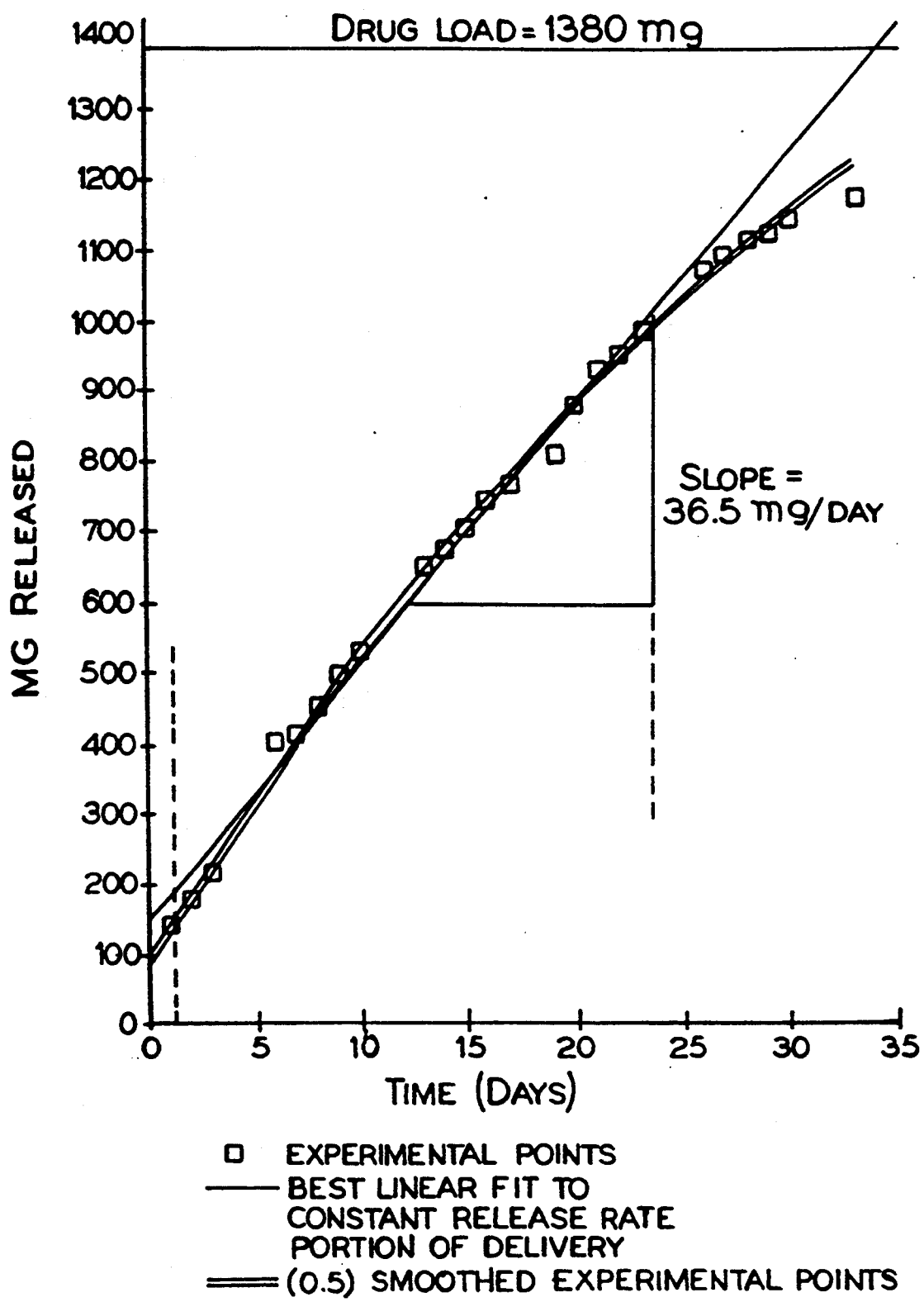
FIG. 2 illustrates the beneficial agent release profile of an exemplary device of this invention.

The average cumulative amount of the drug released from three prototype devices made as described above is shown in FIG. 2. The drug release profile showed three distinct phases. The first phase consisted of a relatively rapid drug release rate which can be considered as initial "burst" of drug. In the second phase, about 70% of the initial drug load was released over a period of about 3 weeks at a relatively constant rate. The third phase was a period of decreasing release rate in which the last 20% of the initial drug load was released. During the constant release period, a drug release rate of 36.5 mg/day was calculated by linear regression.

EXAMPLE 2

Effect of the Initial Drug Load on the Drug Release Rate

Figure 3:
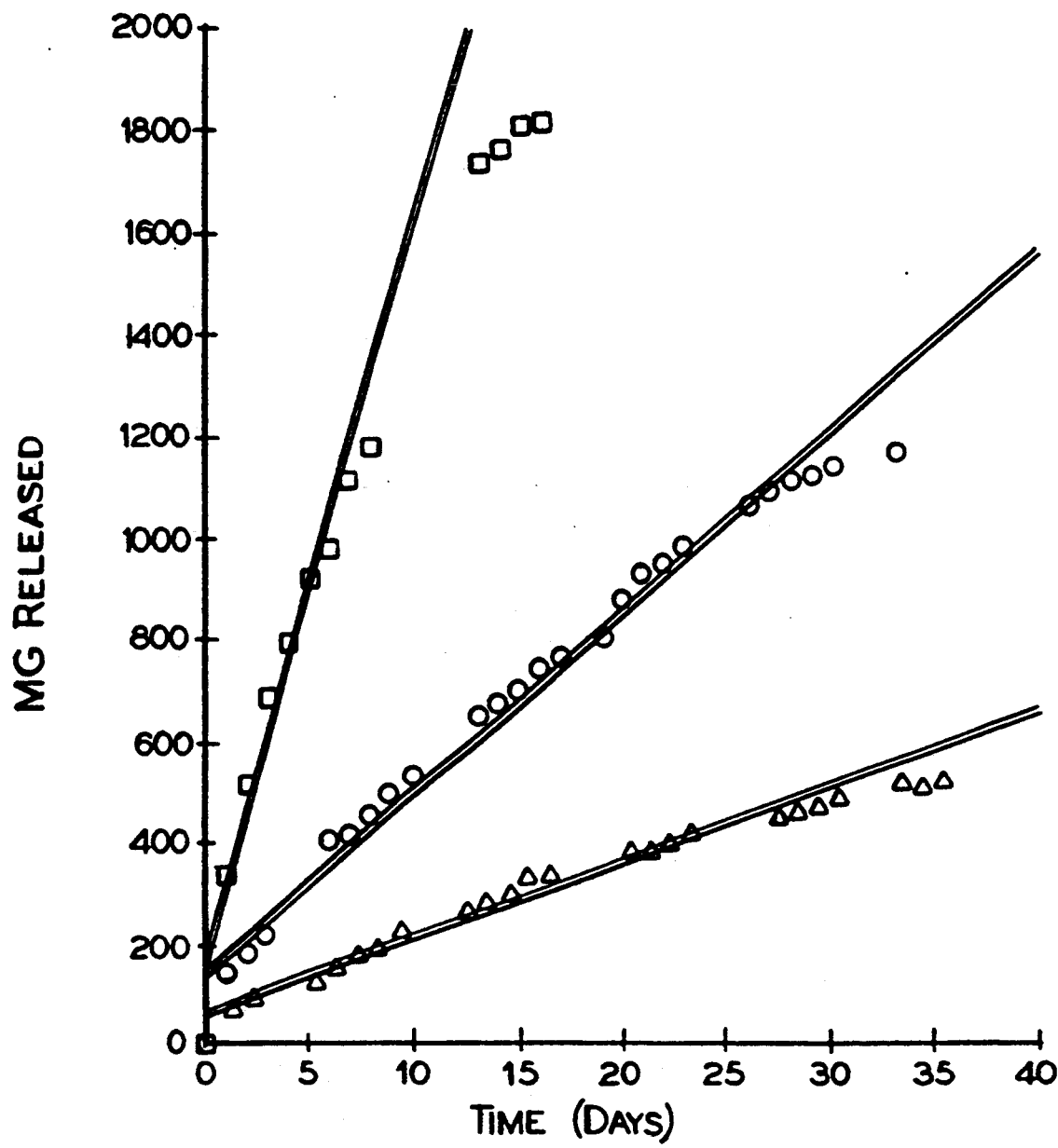
FIG. 3 illustrates the effect of initial beneficial agent concentration on the release profile for modified devices of FIG. 2.
Figure 4:
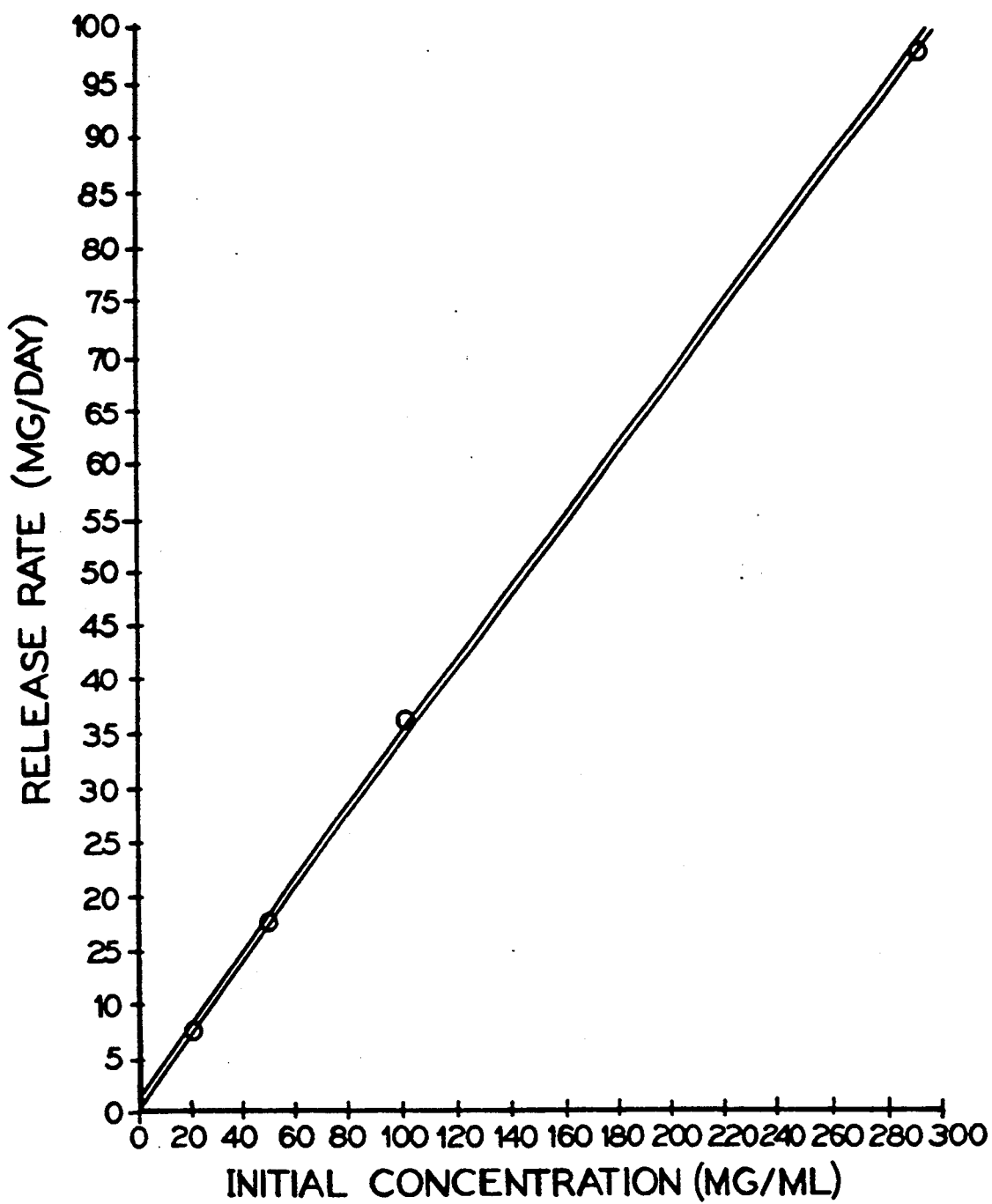
FIG. 4 illustrates the beneficial agent release rate plotted as a function of initial beneficial agent concentration for modified devices of FIG. 2.

Prototype devices were made by the procedure described in Example 2 to study the effect of the initial drug load on the release rate. Thus, the concentration of drug dissolved in the octyl alcohol vehicle ranged from 25 mg/ml to 200 mg/ml. The cumulative drug released from the devices was determined by the procedure described in Example 1. The release rate profiles for three values of the initial drug concentration are shown in FIG. 3. The drug release rates increased with the initial drug concentration in the device. A plot of the drug release rate calculated from the slope of the release profile during the constant release rate or zero-order phase as function of the initial concentration of the drug solution is shown in FIG. 4. The release rates were linearly proportional to the drug concentration and the slope of the regressed straight line was 0.34 ml/day. These observations support the conclusion the drug is released at a volumetric rate of 0.34 ml/day as a solution. Increasing release rates over a desired delivery period can be achieved by increasing the drug load in the deliver device.

EXAMPLE 3

Effect of PE/CTA Membrane Area on the Drug Release Rate

Prototype devices were made as in Example I except that the sintered polyethylene membrane impregnated with cellulose triacetate and wetted with PEG-400 (PE/CTA) present at one end of the device was sandwiched in aluminum discs with holes in the center. These aluminum discs served to occlude some of the disc area which was exposed to the release medium and the drug formulation within the device. Thus, the effective diameter of the PE/CTA membrane disc was varied by using aluminum discs with central holes of an appropriate diameter.

Figure 5:
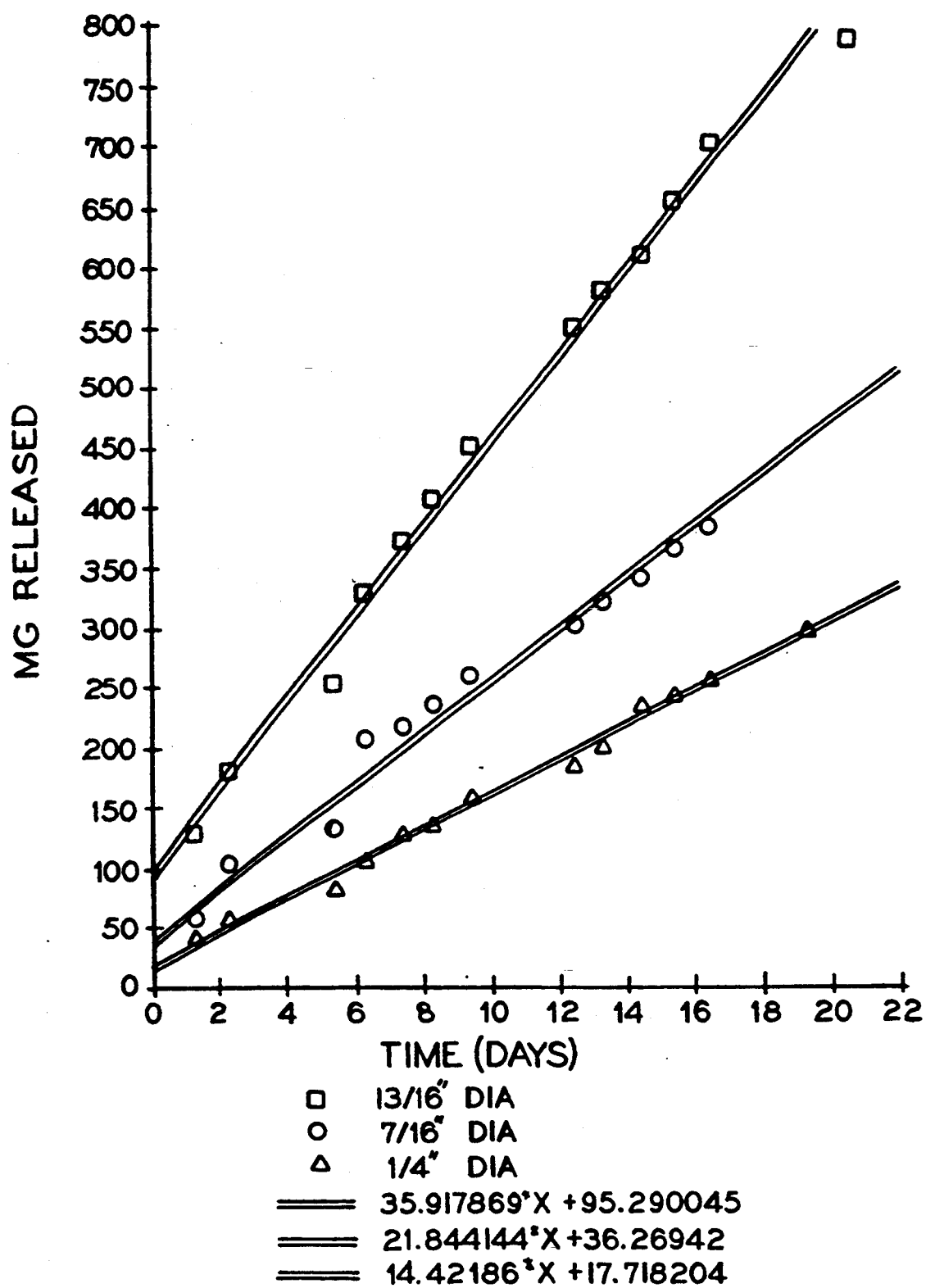
FIG. 5 illustrates the beneficial agent release profile as a function of the beneficial agent-containing hydrophobic medium permeable membrane area for modified devices of FIG. 2.
Figure 6:
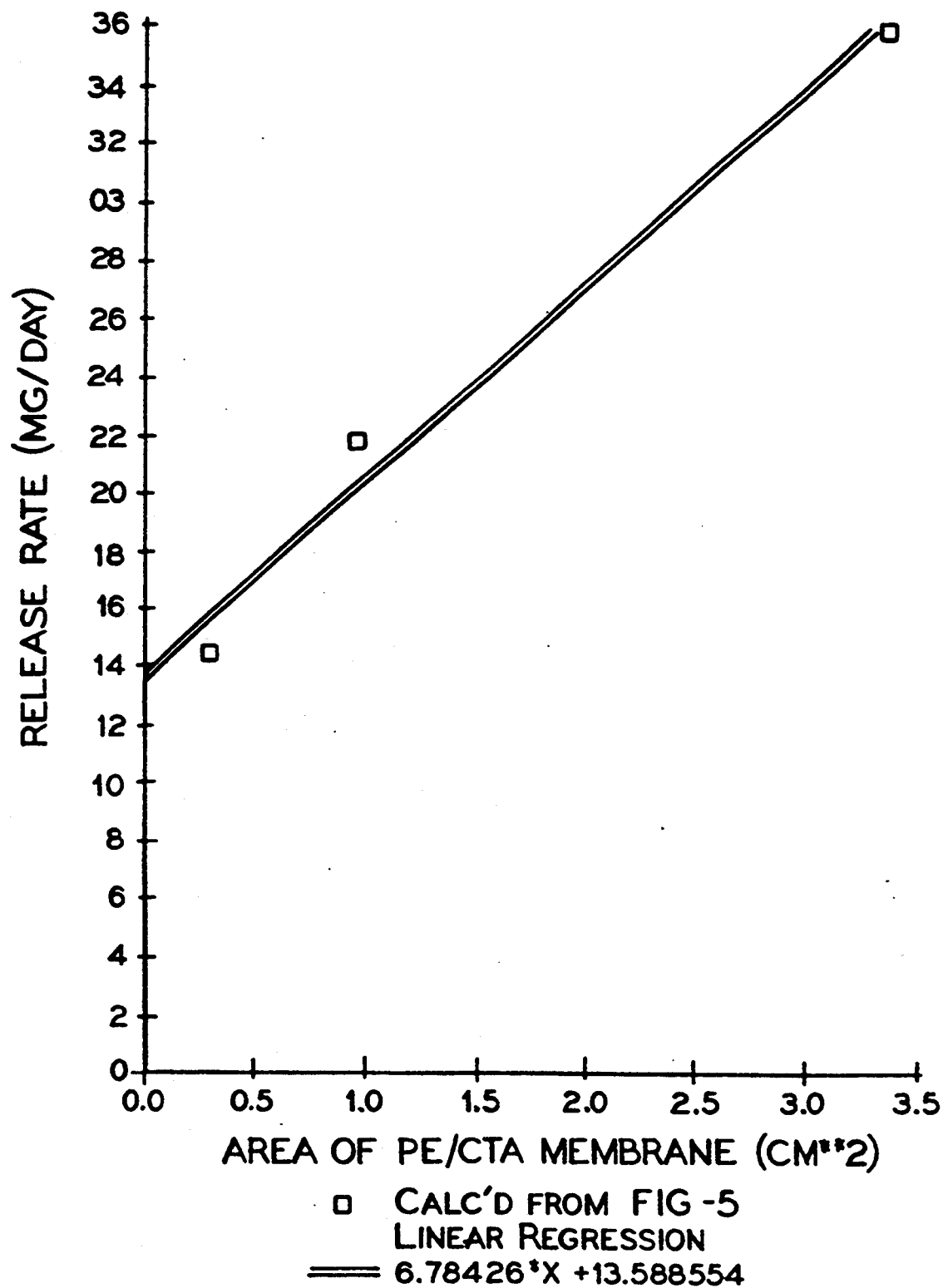
FIG. 6 illustrates the beneficial release rate plotted as a function of beneficial agent-containing hydrophobic medium permeable membrane area for modified devices of FIG. 2.

FIG. 5 shows that the drug release rates are decreased as the effective diameter of the PE/CTA disc is decreased. The total drug load in all cases was 1430 rag. The drug release rates during the constant delivery period were calculated as before and plotted as a function of the exposed (effective) area of the PE/CTA membrane (FIG. 5). The intercept of the best fitting straight line in FIG. 5 was 13.5 rag/day which represents the release rate expected from a hypothetical device with a permeable membrane only at one end.

EXAMPLE 4

Effect of PE Membrane Area on the Drug Release Rate

Prototype devices were made as in example 3 except that instead of occluding the sintered polyethylene membrane impregnated with cellulose triacetate and wetted with PEG-400, the other membrane which was made from sintered polyethylene (PE), was occluded on both sides with the aluminum discs. The release profiles of the ionophore CP-53,607 from these devices were independent of the area of the PE membrane and no differences in the release were seen attributed to a change in the PE membrane area. These observations support the conclusion that the PE membrane is not rate-limiting for the drug release kinetics.

EXAMPLE 5

Effect of Having PE/CTA/PEG-400 Membranes at Both Ends

Prototype devices were made as in Example 1 except that both end membranes of the device consisted of sintered polyethylene discs impregnated with cellulose triacetate and wetted with PEG-400. Drug was not released from these devices. It was concluded from this experimental observation that the PE/CTA/PEG-400 membrane is not permeable to a hydrophobic formulation of the ionophore CP-53,607.

EXAMPLE 6

Effect of Drilling Multiple Moles in the Membrane

Figure 7:
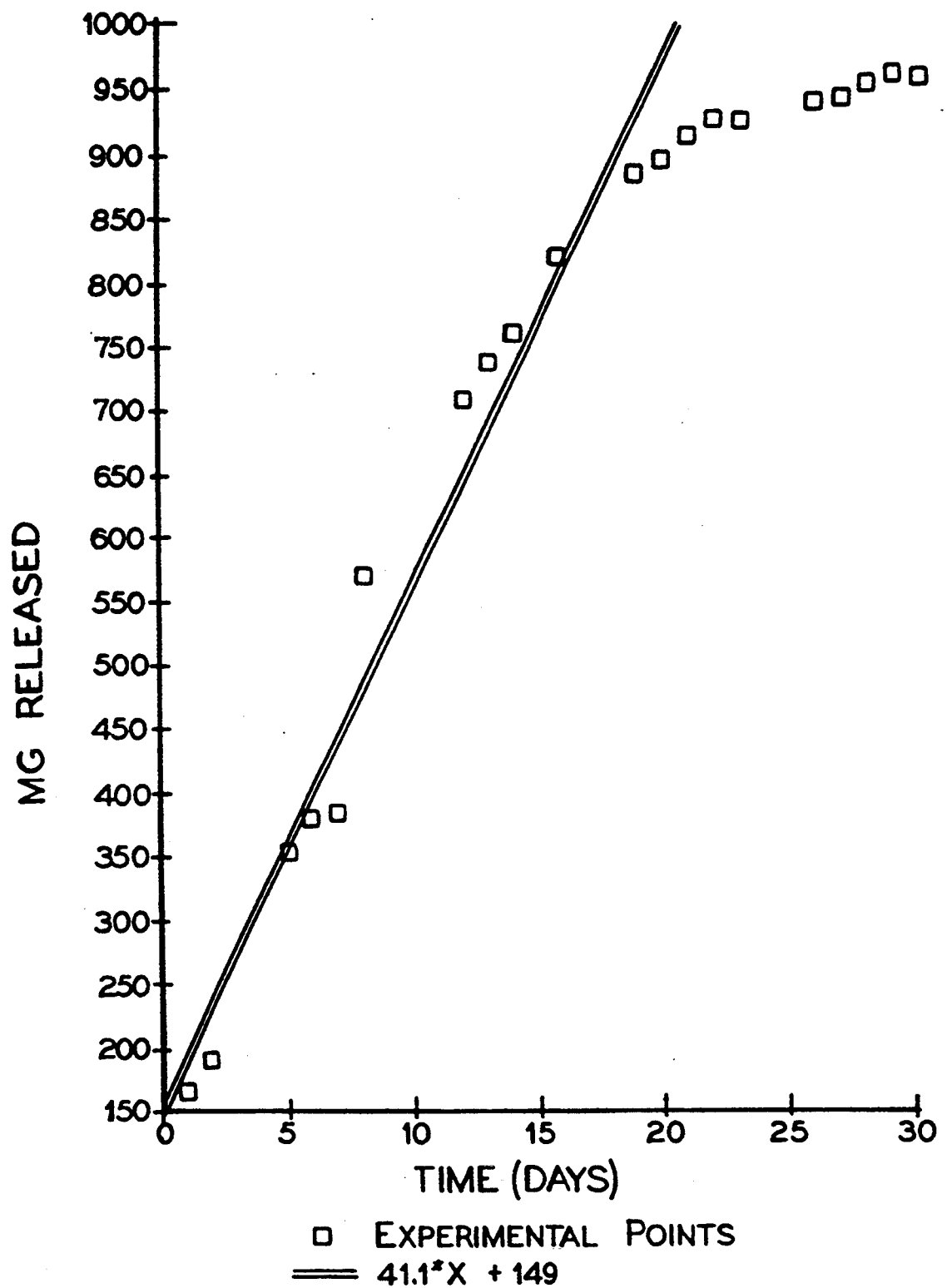
FIG. 7 illustrates the release profile for modified devices of FIG. 2 having holes drilled through the membranes.

Prototype devices were made as in Example 5 except that three, five, or nine holes in a symmetric pattern were drilled in one of the end membranes. The drug release profile for the case in which five holes were drilled in the PE/CTA/PEG-400 membrane is shown in FIG. 7. The average release rate during the constant release rate portion of the delivery profile was 41 rag/day which is consistent with the 36.5 rag/day release rate obtained from devices described in Example 1. It was also concluded that "puncturing" the PE/CTA/PEG-400 disc with holes made this membrane permeable to the drug solution.

EXAMPLE 7

Options for End-Membrane Permeable to Drug

In the previous examples, it was shown that a sintered polyethylene disc without impregnated hydrogel was permeable to the drug formulation and suitable for use in this invention. It was also shown that a sintered polyethylene disc impregnated with a hydrogel such as cellulose triacetate and wetted with PEG-400 was not permeable to the drug solution but could be made permeable by drilling mascroscopic holes through the membrane. This example presents yet another option for the portion of the delivery device which must be permeable to the hydrophobic drug formulation.

Figure 8:
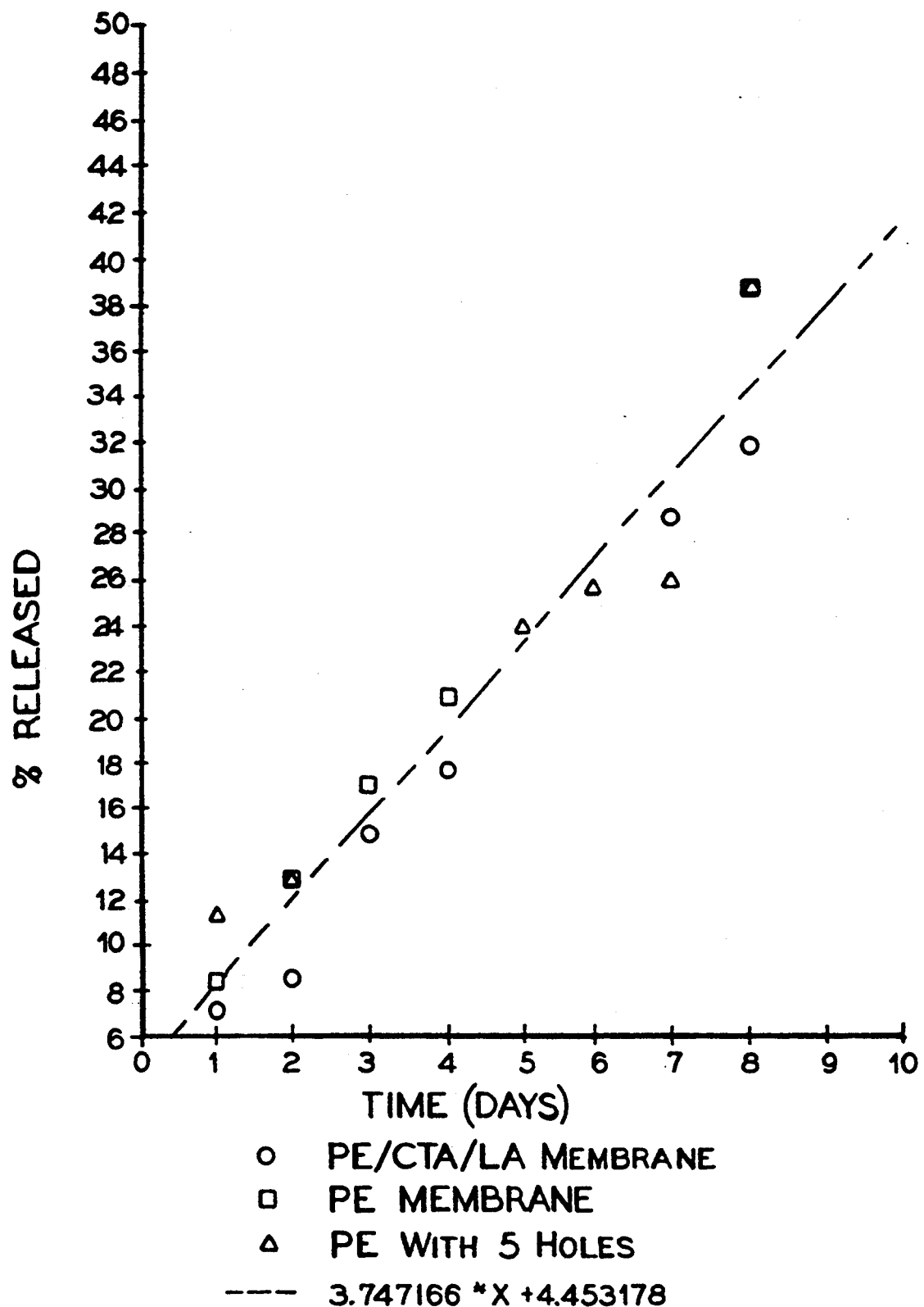
FIG. 8 illustrates the release profile for modified devices of FIG. 2.

Sintered polyethylene discs which were impregnated with cellulose triacetate were "wetted" with a hydrophobic liquid such as lauryl alcohol by immersing the discs into a reservoir of lauryl alcohol and applying suction (negative pressure) to entrap lauryl alcohol in the membrane disc. Prototype devices were made as in Example i and capped with sintered polyethylene disc impregnated with cellulose triacetate and wetted with PEG-400 (PE/CTA/PEG-400) on the end. The other end was capped with a sintered polyethylene disc impregnated with cellulose triacetate and wetted with lauryl alcohol (PE/CTA/LA). FIG. 8 compares the normalized drug release profiles from prototype devices with a PE/CTA/PEG-400 membrane disc at one end and various different membranes, all of which are permeable to the hydrophobic drug formulation, at the other end. The normalized drug release rates were independent of the various membrane types. Since it is highly unlikely that all the different hydrophobic membranes have the same permeability, these data support our conclusion that the membrane permeable to the drug formulation does not directly influence the drug release rate.

EXAMPLE 8

Carriers for Hydrophobic Drugs-Solutions

Figure 9:
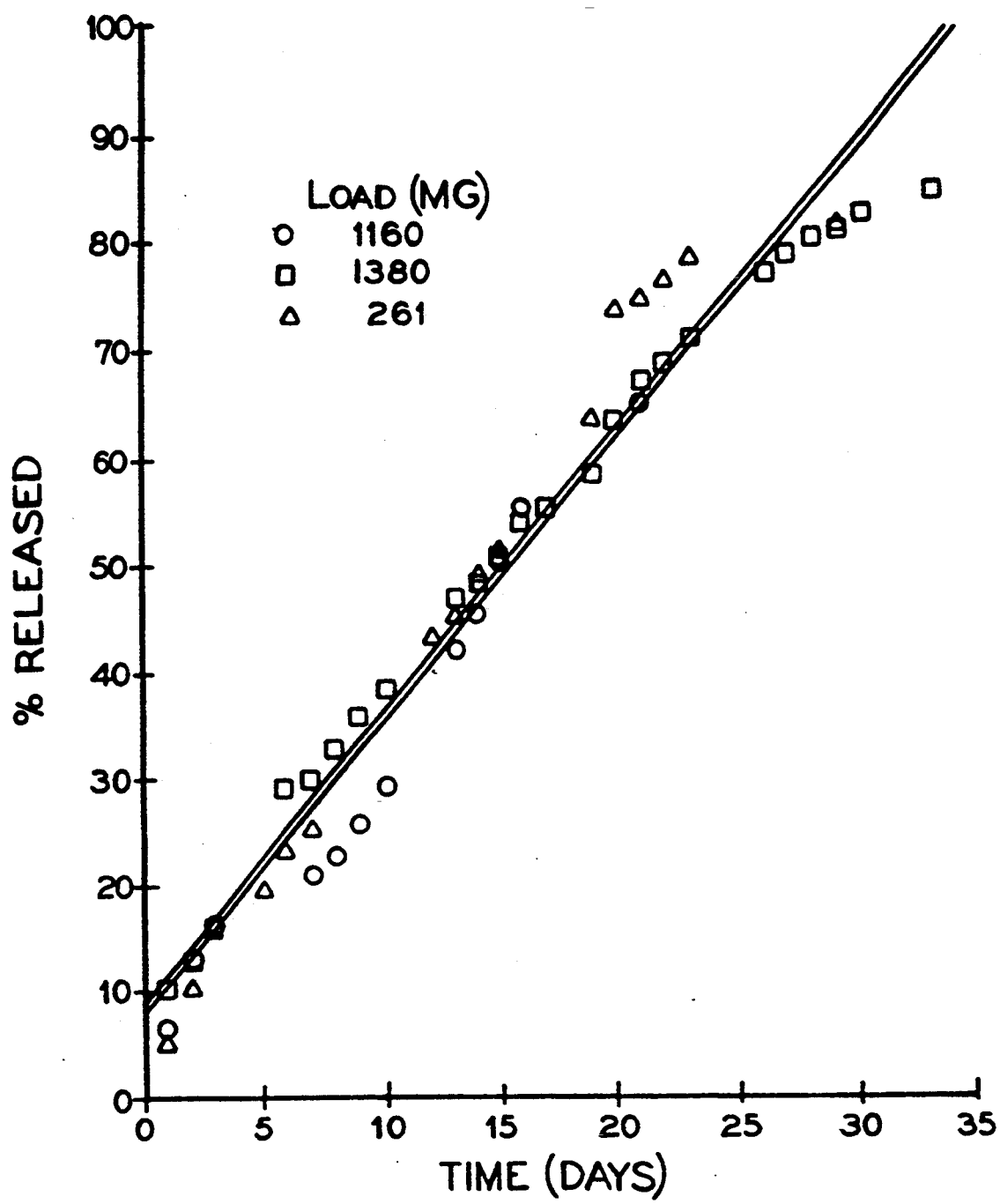
FIG. 9 illustrates the release profile for modified devices of FIG. 2 for different hydrophobic mediums.

Devices were made as in Example 1 using isopropyl myristate, octyl alcohol, lauryl alcohol, or soybean oil as the solvent for the ionophore CP-53-607. The normalized drug release profiles (% of initial drug load released) as a function of time are shown in FIG. 9. The assay procedure for the drug released was either a UV assay or a specific reverse phase HPLC assay depending on our choice of the solvent carrier. It was concluded from the data presented in FIG. 9 that there were no differences in the normalized release rate which could be attributed to the specific solvent carrier used to formulate the drug solution. The actual release rate was dependent on the initial drug concentration (or drug load) as described in Example 2.

EXAMPLE 9

Carriers for Hydrophobic Drugs-Suspension

Prototype devices were made as in Example wherein the drug formulation consisted of a suspension of the drug ionophore CP-53,607 in silicone oil, light mineral oil, or heavy mineral oil, and the swellable polymer was present in the devices as a granular material as opposed to compressed pellets. Although drug was released from these devices, the release rates were erratic and there was,a large device-to-device variability. This was attributed to clogging of the membrane with the swellable polymer, or settling of the drug within the suspension, or both. These experiments did demonstrate that the device of the present invention is capable of delivering a suspension of drug.

EXAMPLE 10

Options for the Swellable Polymer

Figure 10:
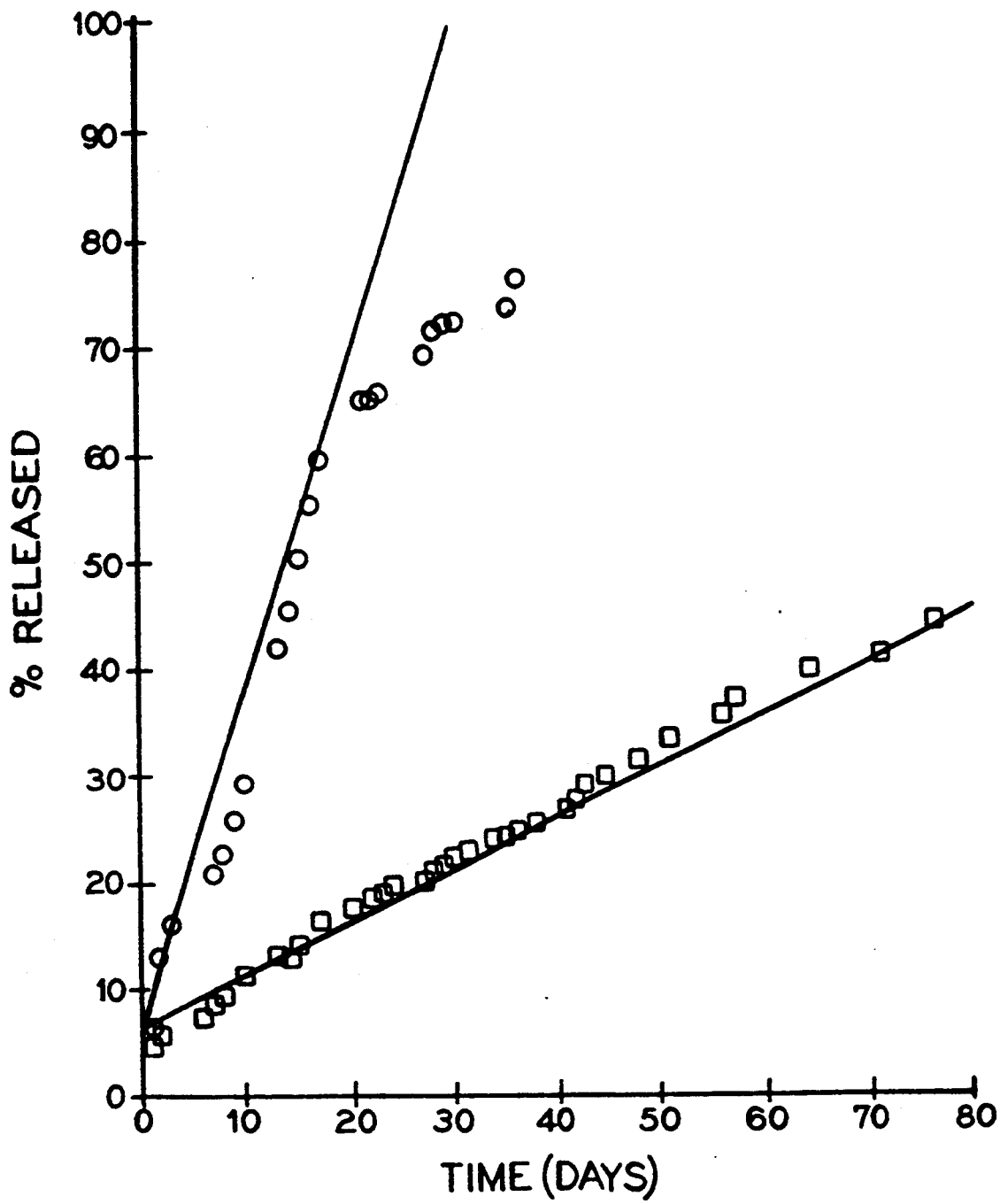
FIG. 10 illustrates the release profile for modified devices of FIG. 2 for different hydrogels.

Prototype devices were made as described in Example 1 with a PE/CTA/PEG-400 membrane at one end of the device and a PE/CTA/LA membrane at the other end containing a solution of the drug in lauryl alcohol and 6 grams of a swellable polymer. Devices with polymers having a range of equilibrium swelling capacity were chosen for this experiment. The normalized drug release profiles for poly (ethylene oxide) and poly(vinyl alcohol) are shown in FIG. 10 and indicate that the drug release rates are affected by the nature of the swellable polymer incorporated into the device, and that it is possible to get drug delivery over several months from devices containing poly(vinyl alcohol) as the swellable polymer.

EXAMPLE 11

Effect of External Temperature

Figure 11:
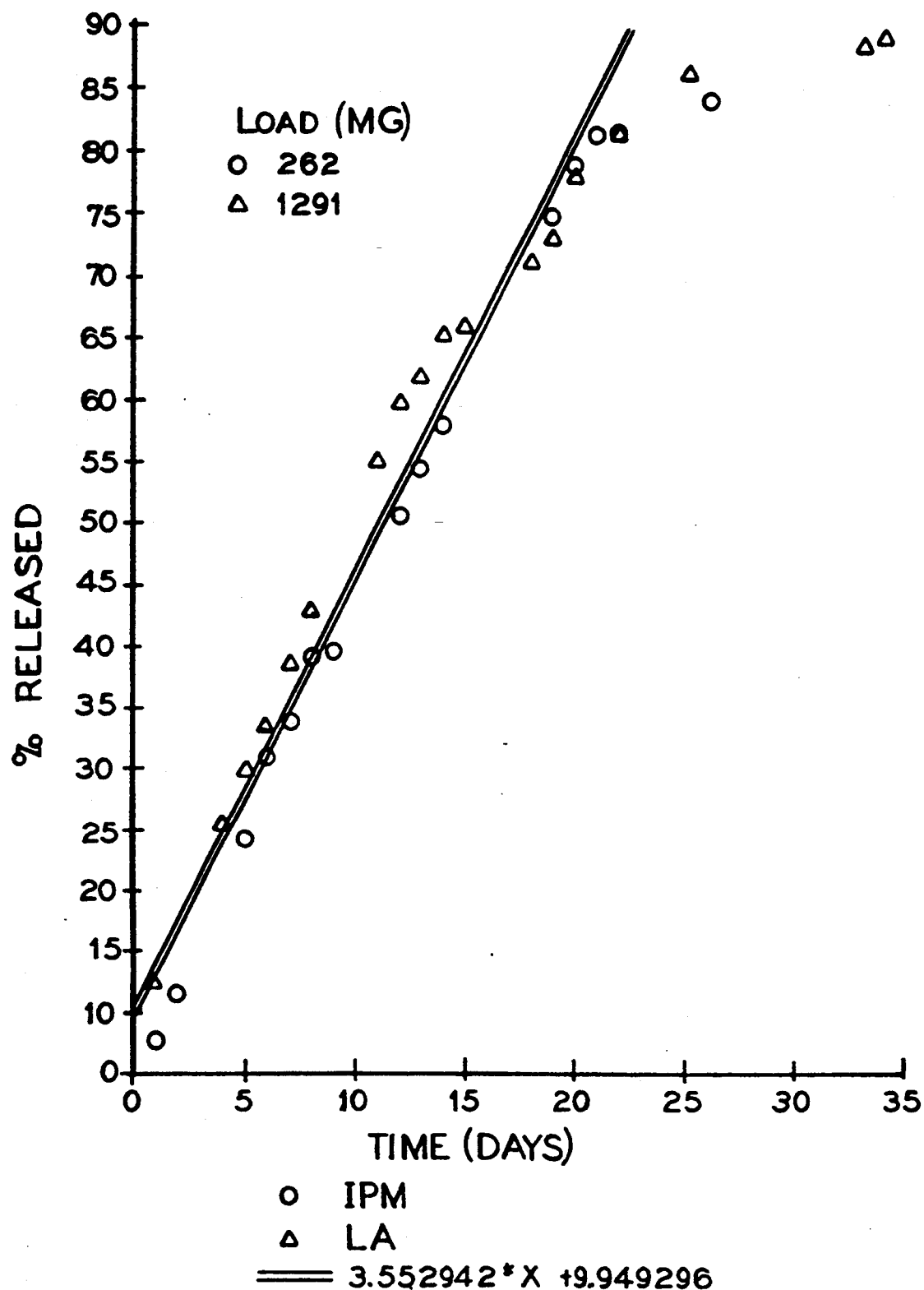
FIG. 11 illustrates the release profile for modified devices of FIG. 2 at 40° C.

Prototype devices were made as described in Example I and the drug solution was formulated as a solution in isopropyl myristate or in lauryl alcohol. The external release medium was kept at a 40° C. compared to ambient temperature (22° C.). Since the shape of the release profile was not altered, it was concluded that the mechanism of the drug release was unchanged as a function of temperature. The amount of drug release for the two devices is shown in FIG. 11.

EXAMPLE 12

Effect of External Hydrodynamics

Prototype devices were made and the release experiments were carried out in flasks as described before. A comparison of the release rate profile with devices shaken using a laboratory shaker versus devices stirred with a magnetic stir-bar revealed that the external hydrodynamics did not effect the release profiles.

EXAMPLE 13

Effect of External pH and Aqueous Dissolution Media

Drug release experiments were conducted using phosphate buffer at pH 9.0, volatile fatty acid buffer at pH 9.0, and volatile fatty acid buffer at pH 5.5. In all cases, the drug release profiles from the prototype devices were not affected by the external pH of the aqueous dissolution medium.

EXAMPLE 14

Release From a Device Made From Clear Plastic

In order to further understand the release mechanism, devices were constructed as described in Example 1 with the following exceptions: (1) The tube containing the swellable polymer and the drug formulation was made from clear plastic which was transparent as opposed to stainless steel, which was opaque, (2) Instead of the unimpregnated disc at one end of the device, a small hole was made in the plastic tube, (3) A small amount of red dye (FD & C #3) was added to the drug solution.

The drug release rate from the device made from clear plastic was the same as that from the equivalent steel prototype. From the observed swelling of the poly(ethylene oxide) placed in the device, it appeared that water from the external medium first entered the device through the hole. The oil soluble dye was not seen being pumped through the hole. This was followed by swelling of the polymer on the membrane-side of the device indicating that water flux was through the PE/CTA/PEG-400 membrane. Within the first day of drug release, the polymer pellets were swollen.

EXAMPLE 15

A device for human health applications based on this invention is made as follows: A two piece capsule shell is constructed of sintered polymer, and either the body or the cap is impregnated with CTA and wetted with PEG-400 while the other is made so that it is permeable to the drug formulation in a hydrophobic medium. The solid polymer and the liquid drug formulation are simultaneously or sequentially filled into the capsule body, the cap is attached and sealed with one of the standard gelatin capsule sealing technologies.

It should be understood that the invention is not limited to the particular embodiments shown and described herein, but that various changes and modifications may be made without departing from the spirit and scope of this novel concept as defined by the following claims.

I claim:

1. A device for controlled delivery of a beneficial agent to an aqueous containing environment, said device comprising: a shaped wall having a thickness of at least 100µm that surrounds and defines an internal reservoir; said wall at least in part permeable to the aqueous environment and said wall formed at least in part of a sintered polymer microporous membrane permeable to a beneficial agent-containing hydrophobic medium when the wall is present in the aqueous containing environment, said sintered polymer impregnated with a low vapor pressure hydrophobic medium; and said reservoir containing a mixture of a hydrophilic swellable composition and said beneficial agent-containing hydrophobic medium, said beneficial agent being insoluble or partially insoluble in said aqueous containing environment.

2. The device as recited in claim 1 wherein said beneficial agent has a solubility more than about one part solute to 1000 part aqueous solvent and less than about one part solute to 30 parts aqueous solvent.

3. The device as recited in claim 2 herein said beneficial agent is soluble in said hydrophobic medium.

4. The device as recited in claim 3 wherein said swellable composition comprises hydrogel and said reservoir contains sufficient hydrogel such that the swelled hydrogel fills at least about 50% of the reservoir.

5. A device for controlled delivery of a beneficial agent to an aqueous containing environment, said device comprising: a shaped wall having a thickness of at least 100µm that surrounds and defines an internal reservoir; said wall at least in part permeable to the aqueous environment and said wall formed at least in part of a sintered polymer microporous membrane permeable to a beneficial agent-containing hydrophobic medium when the wall is present in the aqueous containing environment, said sintered polymer impregnated with hydrogel and wetted with a low vapor pressure hydrophobic medium; and said reservoir containing a mixture of a hydrophilic swellable composition and said beneficial agent-containing hydrophobic medium, said beneficial agent being insoluble or partially insoluble in said aqueous containing environment.

6. A device for controlled delivery of a beneficial agent to an aqueous containing environment, said device comprising: a shaped wall having a thickness of at least 100µm that surrounds and defines an internal reservoir; said wall at least in part permeable to the aqueous environment and said wall formed at least in part of a sintered polymer microporous membrane, said sintered polymer impregnated with a hydrophilic hydrogel wetted with a hydrophilic medium and at least one hole provided therethrough; and said reservoir containing a mixture of a hydrophilic swellable composition and said beneficial agent-containing hydrophobic medium, said beneficial agent being insoluble or partially insoluble in said aqueous containing environment.

7. A device for controlled delivery of a beneficial agent to an aqueous containing environment, said device comprising: a shaped wall having a thickness of at least 100µm that surrounds and defines an internal reservoir; said wall at least in part permeable to the aqueous environment and said wall formed at least in part of a material permeable to a beneficial agent-containing hydrophobic medium when the wall is present in the aqueous containing environment and said wall formed at least in part of a sintered polymer microporous membrane permeable to the aqueous containing environment, said sintered polymer impregnated with a low vapor pressure hydrophilic medium; and said reservoir containing a mixture of a hydrophilic swellable composition and said beneficial agent-containing hydrophobic medium, said beneficial agent being insoluble or partially insoluble in said aqueous containing environment.

8. A device for controlled delivery of a beneficial agent to an aqueous containing environment, said device comprising: a shaped wall having a thickness of at least 100µm that surrounds and defines an internal reservoir; said wall at least in part permeable to the aqueous environment and said wall formed at least in part of a material permeable to a beneficial agent-containing hydrophobic medium when the wall is present in the aqueous containing environment and said wall formed at least in part of a sintered polymer microporous membrane permeable to the aqueous containing environment, said sintered polymer impregnated with a hydrogel and wetted with a low vapor pressure hydrophilic medium; and said reservoir containing a mixture of a hydrophilic swellable composition and said beneficial agent-containing hydrophobic medium, said beneficial agent being insoluble or partially insoluble in said aqueous containing environment.

9. A device for controlled delivery of a beneficial agent to an aqueous containing environment, said device comprising: a shaped wall having a thickness of at least 100 µm that surrounds and defines an internal reservoir; said wall at least in part permeable to the aqueous environment and said wall formed at least in part of a material permeable to a beneficial agent-containing hydrophobic medium when the wall is present in the aqueous containing environment; and said reservoir containing sufficient air to achieve a predetermined time lag release and a mixture of a hydrophilic swellable composition and said beneficial agent-containing hydrophobic medium, said beneficial agent being insoluble or partially insoluble in said aqueous containing environment.

* * * * *